United States Patent [19]

Honkanen

[11] Patent Number: 4,712,545
[45] Date of Patent: Dec. 15, 1987

[54] SURGICAL INSTRUMENT

[75] Inventor: George P. Honkanen, Scituate, Mass.

[73] Assignee: Acufex Microsurgical, Inc., Norwood, Mass.

[21] Appl. No.: 904,949

[22] Filed: Sep. 5, 1986

Related U.S. Application Data

[63] Continuation of Ser. No. 596,923, Apr. 5, 1984, abandoned.

[51] Int. Cl.$^4$ .................. A61B 17/28; A61B 17/32
[52] U.S. Cl. .................................. 128/305; 128/321; 128/751
[58] Field of Search ............... 128/751, 321, 322, 312, 128/319, 305, 318; 16/355, 356

[56] References Cited

U.S. PATENT DOCUMENTS

| | | | |
|---|---|---|---|
| 1,754,806 | 4/1930 | Stevenson | 128/318 |
| 1,962,709 | 6/1934 | Case | 16/355 X |
| 4,043,343 | 8/1977 | Williams | 128/321 |
| 4,123,822 | 11/1978 | Bentley | 16/355 |
| 4,369,788 | 1/1983 | Goald | 128/321 |
| 4,390,019 | 6/1983 | Le Veen | 128/325 |
| 4,396,021 | 8/1983 | Baumgartner | 128/754 |

FOREIGN PATENT DOCUMENTS

| | | | |
|---|---|---|---|
| 844129 | 5/1952 | Fed. Rep. of Germany | 128/321 |
| 1504811 | 12/1967 | France | 16/355 |
| 1279003 | 6/1972 | United Kingdom | 128/321 |
| 1315200 | 4/1973 | United Kingdom | 16/355 |

OTHER PUBLICATIONS

Advertisement by V. Mueller and Co., from *Surgery, Gynecology & Obstetrics*, vol. 89, No. 3 (8-1941).

*Primary Examiner*—Michael H. Thaler
*Attorney, Agent, or Firm*—Schiller, Pandiscio and Kusmer

[57] ABSTRACT

A surgical tool of the type comprising a first stationary jaw member and a second movable jaw member adapted for pivotal movement towards and away from the first stationary jaw member, wherein the second movable jaw member is attached to the first stationary jaw member by a first arcuate lug and groove arrangement, and the second movable jaw member is also attached to a coupling member by a second lug and groove arrangement, in order that when the coupling member is moved in a first direction relative to the first stationary jaw member, the second movable jaw member will open away from the first stationary jaw member, and when the coupling member is moved in a second opposite direction relative to the first stationary jaw member, the second movable jaw member will close towards the first stationary jaw member. The invention may take the form of surgical punches or surgical forceps. A novel locking means is provided for the surgical forceps.

43 Claims, 21 Drawing Figures

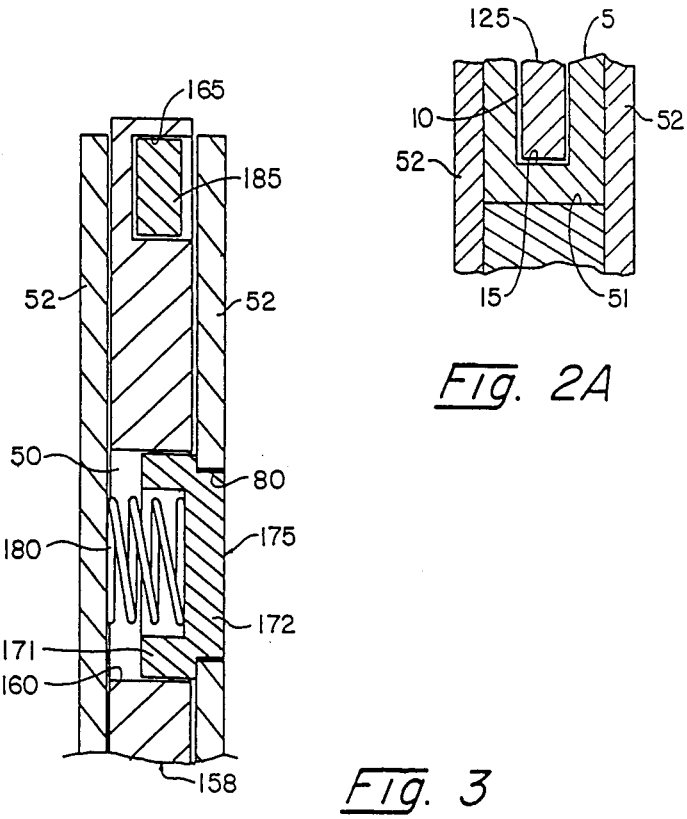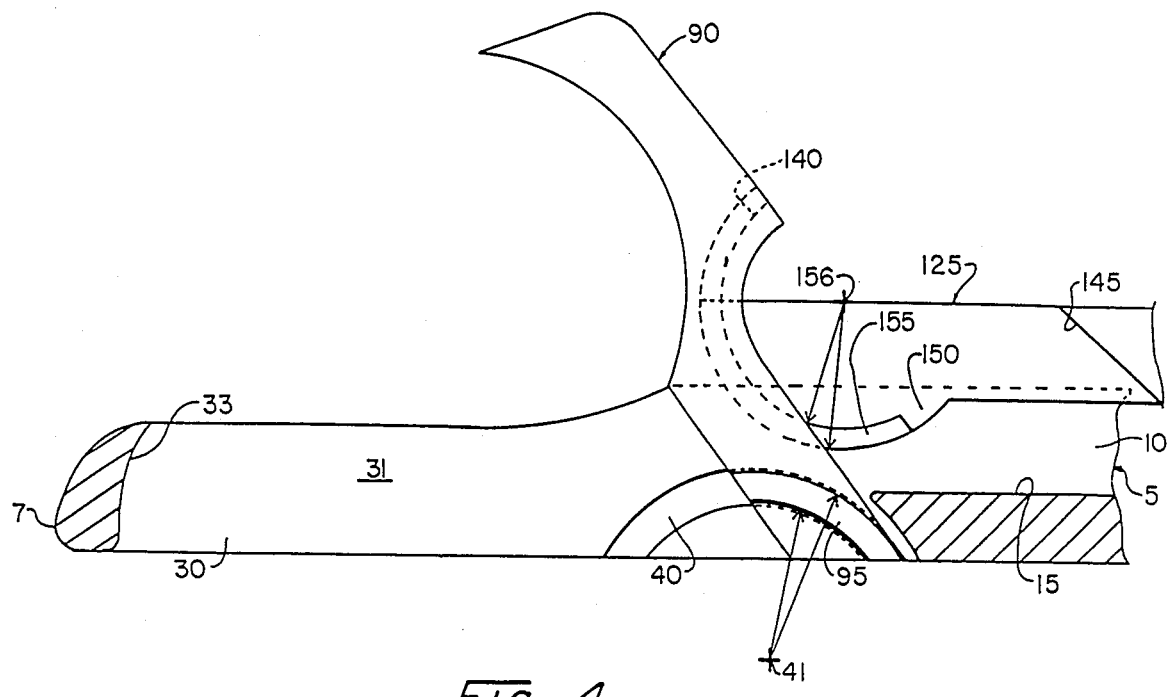

SURGICAL INSTRUMENT

This application is a continuation of application Ser. No. 596,923 filed Apr. 5, 1984, now abandoned.

FIELD OF THE INVENTION

This invention relates to surgical instruments in general, and more particularly to surgical punches and surgical forceps.

BACKGROUND OF THE INVENTION

Surgical punches are well known in the art. Such instruments are generally used in arthroscopic surgery to cut through tough body tissue (e.g. cartilage) in areas of limited access (e.g. knee interiors). Surgical punches cut by punching out pieces of tissue. To this end, surgical punches generally comprise first and second jaw members, wherein the first jaw member is stationary and serves as a die, and the second jaw member is mounted for pivotal movement towards and away from the first jaw member and serves as a punch. In the typical surgical punch, the two jaw members are adapted to be alternately opened and closed relative to one another by manipulation of a scissors-type handle.

Unfortunately, conventional surgical punches have exhibited one or more limitations during use. More particularly, conventional surgical punches typically utilize a relatively inefficient mechanical design in which the punch's pivot points are subjected to significant stress during use. Such stress may shorten the lifetime of the surgical punch. The foregoing stress problem is exacerbated by the fact that conventional surgical punches typically use tiny pivot pins to hinge the two jaw members together. Such pivot pins have proven susceptible to breakage during use, thereby rendering the surgical punches inoperable or, even worse, resulting in tiny fragments of metal entering the surgical area. Attempts have been made to solve this breakage problem by increasing the dimensions of selected parts of the surgical punches so as to increase part strengths; however, such efforts have not been wholly successful, inasmuch as the increased dimensions tend to render the instruments less satisfactory for use in cramped working reas (e.g. knee interiors). Efforts have also been made to solve the aforementioned problems by producing surgical punches which do not use pivot pins. However, such other arrangements have not been entirely satisfactory.

Surgical forceps are also well known in the art. Such instruments are used to grasp tissue and/or objects that would be inconvenient or impractical to grasp by hand. Surgical forceps generally comprise first and second jaw members, with one or both of the jaw members being adapted for pivotal movement towards and away from the other jaw member. In the typical forceps design, the two jaw members are adapted to be alternately opened and closed relative to one another by manipulation of a scissors-type handle. Such forceps may also include some sort of means for locking the first and second jaw members in a selected position for an extended period of time.

Conventional surgical forceps frequently have the same limitations as surgical punches, e.g. excessive stress at pivot points leading to early failure, or excessive size which hampers their use in cramped working areas. A further problem with some prior forceps designs is that their locking means have a tendency to slip out of a selected setting. If the jaws are spring biased so as to open, the jaws will tend to open to a wider setting when the looking means slips.

OBJECTS OF THE INVENTION

Accordingly, one of the objects of the present invention is to produce a surgical punch which is extremely durable and able to withstand significant stress during use without failing.

Another object is to produce a surgical punch which utilizes a relatively efficient mechanical design, so as to minimize the stress on its pivot points during use.

Another object is to produce a surgical punch which does not employ pivot pins in its construction.

Still another object is to produce a surgical punch which is small in size and able to work well in confined spaces.

A further object is to provide a surgical punch which is designed so that its cutting action is a combination of shearing and cutting, rather than just shearing alone.

Yet another object is to produce surgical forceps which utilize a relatively efficient mechanical design, so as to minimize the stress on its pivot points during use.

A further object is to produce surgical forceps which are small in size, and able to work well in confined spaces.

And another object is to produce surgical forceps having novel means for securely locking the forceps in a selected clamping position for an extended period of time.

Still another object is to produce forceps which may be adapted for use in areas other than the medical field, e.g. in the electronics industry, the jewelry industry, etc.

SUMMARY OF THE INVENTION

These and other objects are achieved by a novel tool which comprises a first stationary jaw member and a second movable jaw member, wherein the second movable jaw member is attached to the first stationary jaw member by a first arcuate lug and groove arrangement so as to be capable of pivotal movement towards and away from the first stationary jaw member, and further wherein the second movable jaw member is attached to a coupling member by a second arcuate lug and groove arrangement, in order that when the coupling member is moved in a first direction relative to the first stationary jaw member, the second movable jaw member will open away from the first stationary jaw member, and when the coupling member is moved in a second opposite direction relative to the first stationary jaw member, the second movable jaw member will close towards the first stationary jaw member, whereby (a) when the first and second jaw members are adapted for cutting applications, body tissue interspaced between the first and second jaw members may be severed in a punching motion as the jaw members are opened and closed relative to one another by movement of the coupling member relative to the first stationary jaw member, and (b) when the first and second jaw members are adapted for gripping applications, body tissue and/or objects interspaced between the first and second jaw members may be grasped therebetween as the jaw members are opened and closed relative to one another by movement of the coupling member relative to the first stationary jaw member. In the preferred embodiment of the invention, the first stationary jaw member is attached to one arm of a scissors-type handle and the coupling member is attached to the second arm of the scissors-type handle, so that the jaw members may be made to close and open relative to one another simply by moving the two arms of the scissors-type handle towards and away from one another.

BRIEF DESCRIPTION OF THE DRAWINGS

Still other objects and features of the present invention will be more fully disclosed or rendered obvious in the following detailed description of the preferred embodiment, which is to be considered together with the accompanying drawings wherein like numbers refer to like parts and further wherein:

FIG. 2A is a sectional view in elevation taken along line 2A—2A of FIG. 2;

FIG. 3 is a sectional view taken along line 3—3 of FIG. 2;

FIG. 4 is an enlarged fragmentary side elevation partially in section of the front portion of the same surgical punch in its open position;

DETAILED DESCRIPTION OF THE PREFERRED EMBODIMENT

Figure 1:
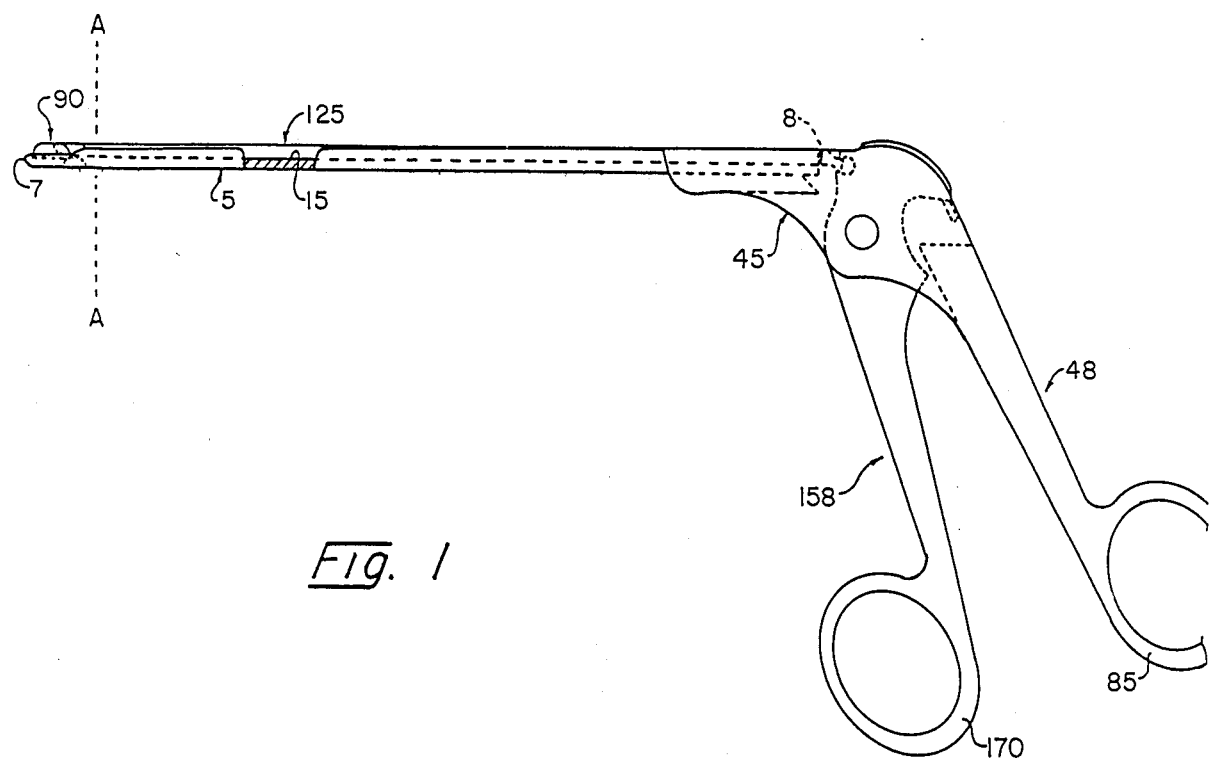
FIG. 1 is an elevational view, partly in section, of the left side of a surgical punch which constitutes a preferred embodiment of the present invention, with the punch being shown in its closed position.
Figure 6:
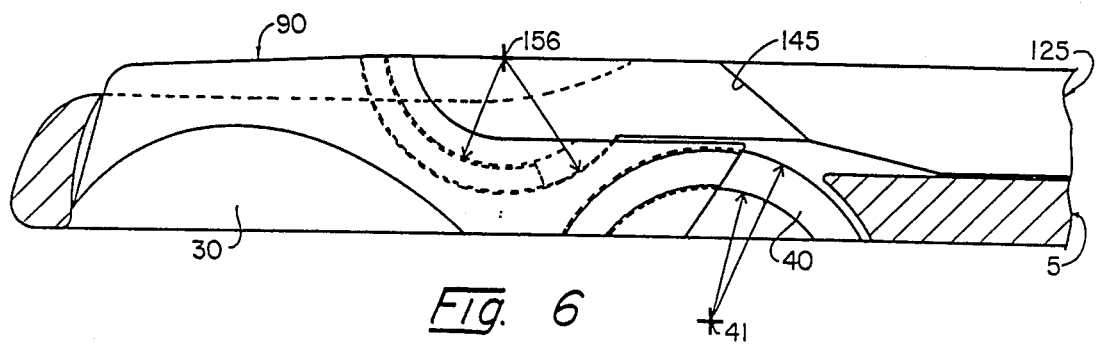
FIG. 6 is an enlarged side elevation partially in section of the front portion of the same punch in its closed position.
Figure 7:
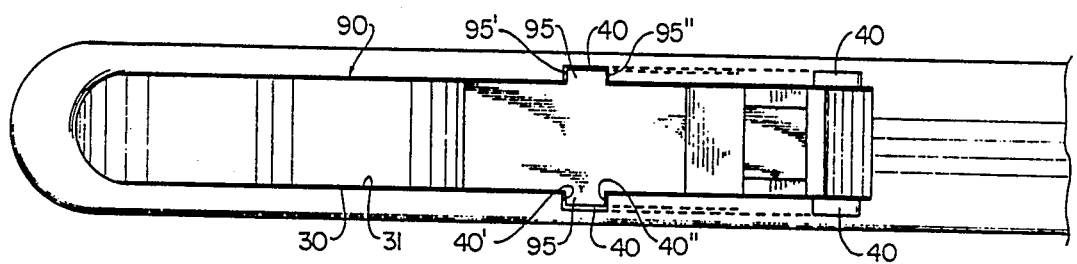
FIG. 7 is an enlarged bottom plan view of the front portion of the same punch in its closed position.
Figure 5:
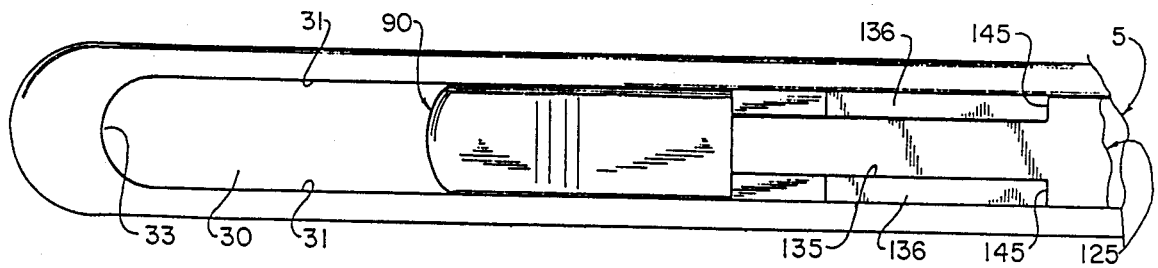
FIG. 5 is an enlarged top plan view of the front portion of the same punch in its open position.

Looking first at FIG. 1, the illustrated embodiment of the surgical punch comprises a first stationary jaw member 5 which is substantially rod-like in nature. For convenience of description, a broken line A—A has been included in FIG. 1 in intersecting relation with jaw member 5. The portion of jaw member 5 extending between line A—A and the jaw member's front tip 7 is considered to be its front section. The rear section of the jaw member extends between line A—A and the jaw member's rear surface 8. The rear section of jaw member 5 has a substantially uniform cross-section along its length, and it includes a top groove 10 which defines a floor 15 (FIGS. 1, 2, 2A and 4). The front section of jaw member 5 is reduced in height relative to its rear section (FIGS. 1 and 4), and includes a vertical opening 30 (FIGS. 4, 5, 6 and 7). Opening 30 extends completely through first jaw member 5, and intersects the front end of top groove 10 (FIG. 4). The inner side surfaces 31 of jaw member 5, which form the sides of opening 30, are flat (FIGS. 4 and 5). The outer surfaces of the front section of jaw member 5 which are disposed about the upper perimeter of opening 30 are sloped so as to form substantially knife-like edges at the upper perimeter of side surfaces 31 and the surface 33 at the front side of opening 30. A pair of first arcuate grooves 40 are disposed in the two inner side surfaces 31 which form the sides of opening 30 (FIGS. 4, 6 and 7). Grooves 40 are aligned with one another. Each first groove 40 comprises a segment of a circular arc having its center point below and exterior to jaw member 5. The location of the center point of the first groove 40 shown in FIG. 4 is marked by a "+" symbol and is identified by the reference numeral 41.

Looking now at FIGS. 1, 2, 2A and 3, first stationary jaw member 5 is securely attached to the upper portion 45 of a first arm 48 of a scissors-type handle. Upper portion 45 of arm 48 has an irregularly-shaped central opening 50 (FIGS. 2 and 3) and a top slot 51 (FIGS. 2 and 2A) which intersects opening 50. Opening 50 and slot 51 divide upper portion 45 into two side sections 52. Opening 50 is shaped so as to form a pair of lower shoulders 55 and 60 and a pair of upper shoulders 70 and 75. Upper portion 45 of arm 48 also has a hole 80 (FIG. 3) which passes through the right side wall section 52 so as to intercept central opening 50. First arm 48 has a finger grip 85 (FIG. 1). First stationary jaw member 5 is located in slot 51 and is securely attached to upper portion 45 of arm 48 so that the inner end of the jaw member extends into the arm's central opening 50 and rests on the base surface of slot 51, and also so that the jaw member's top groove 10 communicates with the arm's central opening 50. Jaw member 5 is fixed in place by ways well known in the art, e.g. by brazing, so that jaw member 5 and arm 48 form a single unit.

Looking now at FIGS. 1, 4, 5 and 7, the preferred embodiment of the invention also comprises a second movable jaw member 90. Jaw member 90 is pivotally attached to first stationary jaw member 5. More particularly, second movable jaw member 90 is sized with its front and side outer surfaces nearly engaging the corresponding inner surfaces 31 and 33 of the front section of jaw member 5 at opening 30 so that it can be received in opening 30 of stationary jaw member 5 (FIG. 6), and it includes a pair of first arcuate flanges 95 on its two outer side surfaces (FIGS. 4 and 7). Flanges 95 project outward from the aforementioned side surfaces of jaw member 90 and are sized and have a radius of curvature such as to cause them to make a close sliding fit in arcuate grooves 40 of stationary jaw member 5. Flanges 95 and grooves 40 together form a first arcuate lug and groove arrangement which allows the second movable jaw member 90 to be moved in a pivoting manner about the imaginary central axis of arcuate grooves 40, whereby second movable jaw member 90 can be pivoted between an open position (FIG. 4) wherein the forward tip of movable jaw member 90 is raised and completely removed from opening 30, and a closed position (FIG. 6) wherein the forward tip of second movable jaw member 90 is in a down position within opening 30. In this way, the first stationary jaw member 5 can function as a die, and the second movable jaw member 90 can function as a punch, for the purpose of cutting through tissue with a punching motion. Movable jaw member 90 has its side surfaces, its front surface, and its bottom surfaces appropriately sloped so that they form substantially knife-like edges at their intersections. These knife-like bottom edges on movable jaw member 90 cooperate with the aforementioned knife-like upper edges of the surfaces 31 and 33 of the stationary jaw member 5 so as to facilitate severing of any tissue which may be disposed between the two jaw members as the two jaw members are closed relative to one another.

Figure 2:
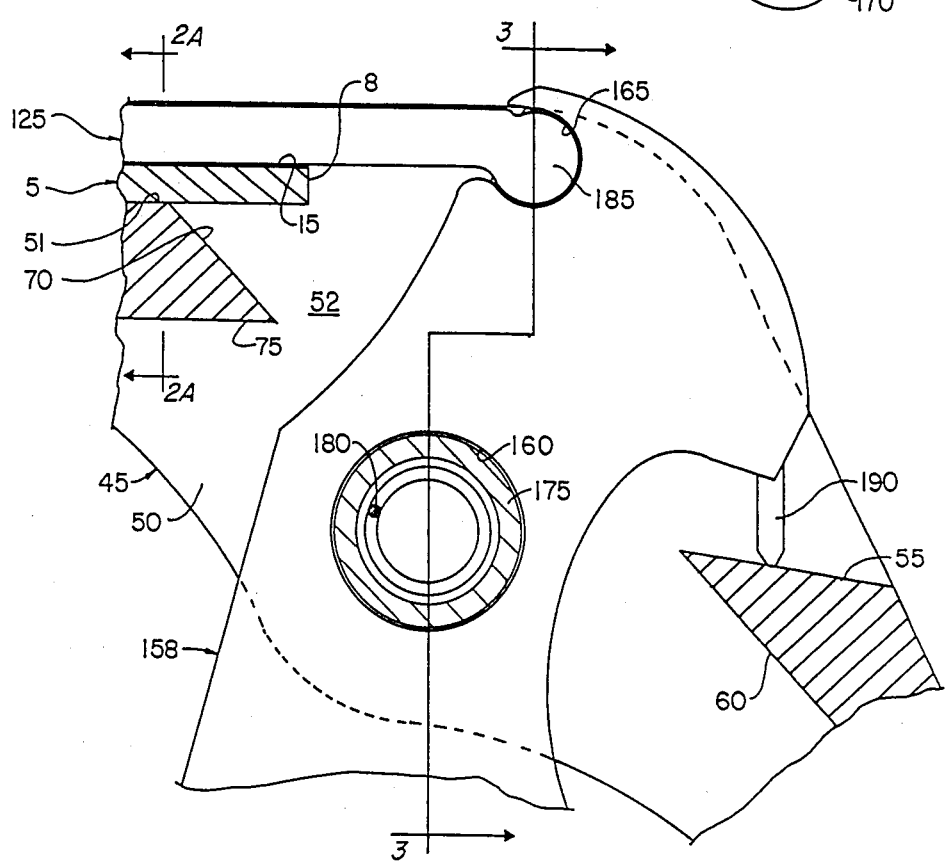
FIG. 2 is an enlarged fragmentary side elevation partially in section of the central or hinge portion of the same surgical punch, but with the punch in its open position.

Looking now at FIGS. 1, 2, 2A, 4 and 5, movable jaw member 90 is adapted to be opened and closed relative to stationary jaw member 5 by a coupling member 125. Movable jaw member 90 is provided with a groove-like recess 135 in its rear upper surface (FIG. 5) so as to form two parallel wall portions 136. The latter have opposed arcuate grooves 140 (FIG. 4) disposed on opposite sides of recess 135 in opposing relation. Coupling member 125 has a uniform, substantially rectangular cross-section along the majority of its length, thereby allowing it to be slidably received in groove 10 as shown in FIGS. 2 and 2A. However, near its front end, coupling member 125 is narrowed in width, so as to provide a pair of sloped shoulders 145 (FIGS. 4 and 5), so that the portion of the coupling member forward of shoulders 145 can be slidably received in the second jaw member's groove-like recess 135 (FIG. 5). In addition to the foregoing, coupling member 125 is provided with an enlarged rounded nose section 150 at its front end (FIG. 4). Nose section 150 includes a pair of oppositely projecting, like second arcuate flanges 155 (FIG. 4). Flanges 155 extend about the curved perimeter of nose section 150. Each second flange 155 comprises a segment of a circular arc having its center point at approximately the top surface of coupling member 125, at the center point of enlarged nose section 150. The location of the center point of the second flange 155 shown in FIG. 4 is marked with a "+" symbol and is identified by the reference numeral 156. These second flanges are appropriately sized and spaced so as to be received in and mate with the aforementioned arcuate grooves 140 of second moving jaw member 90. Flanges 155 and grooves 140 together form a second arcuate lug and groove arrangement permitting pivotal movement between jaw member 90 and coupling member 125. As a consequence of the foregoing construction, second movable jaw member 90 may be moved back and forth in a pivoting manner about the imaginary central axis of first arcuate grooves 40 so as to be alternatively opened and closed relative to first stationary jaw member 5, simply by moving coupling member 125 alternately back and forth in a substantially linear fashion within top groove 10 of stationary jaw member 5. In this respect, it is to be appreciated that inasmuch as the axis upon which first arcuate flanges 95 pivot is significantly spaced from the axis upon which second arcuate flanges 155 pivot, significant mechanical advantage is obtained as coupling member 125 actuates second movable jaw member 90.

Looking next to FIGS. 1, 2 and 3, coupling member 125 is adapted to be moved back and forth within groove 10 of first stationary jaw member 5 by the second arm 158 of the scissors-type handle. To this end, arm 158 has a pivot hole 160 and a rounded notch 165 formed in its upper end, and a finger grip 170 formed in its lower end. The upper end of arm 158 is received in central opening 50 of first arm 45 and is positioned so that its hole 160 is aligned with the hole 80 of arm 48. Hole 160 is sized larger than hole 80, in order that second arm 158 may be rotatably pinned to first arm 48 by a stud 175 and a spring 180, in the manner shown in FIG. 3. Stud 175 has a head 171 sized to fit in hole 160 and a reduced diameter shank 172 sized to fit in hole 80. Rounded notch 165 is sized so that it will rotatably receive and hold a corresponding bulbous extension 185 formed on the rear end of coupling member 125 (FIGS. 2 and 3). As a result of the foregoing construction, it will be seen that as finger grips 85 and 170 of the scissors-type handle are alternately moved away from and towards one another, second movable jaw member 90 can be made to respectively open and close with regard to first stationary jaw member 5. A fixed stop member 190 on arm 158 (FIG. 2) serves to limit the pivoting movement of arm 158 relative to arm 48 through its engagement with shoulder 55. In addition, pivotal movement of arm 158 relative to arm 48 is limited by engagement of arm 158 with shoulder 70.

Looking next at FIGS. 8-12, there is shown surgical forceps constructed in accordance with the present invention. The surgical forceps are substantially the same as the surgical punch just described, except for two significant differences which are hereinafter discussed.

The first significant difference (illustrated in FIGS. 9 and 10) involves the front section of the instrument. Inasmuch as the forceps are intended to grip tissue and/or objects, rather than sever tissue, the two jaw members have been constructed in a manner slightly different from the ones used in the surgical punch. More particularly, first stationary jaw member 5A has a blind hole or recess 30A rather than a through hole. Furthermore, the first arcuate grooves 40A are not disposed in side walls 31A of opening 30A. Instead, grooves 40A are formed in the side walls of a through opening 35A which is separated from blind opening 30A by a series of stepped surfaces 38A. In addition to the foregoing, first stationary jaw member 5A includes a plurality of tiny teeth 32A on the upper edges of its two side walls 31A and on wall 33A defining the front side of opening 30A.

Second movable jaw member 90A is in turn provided with a recess 91A which compliments the recess 31A in stationary jaw member 5A. Jaw member 90A includes a flat surface 92A disposed about the perimeter of recess 91A and adapted to mate with teeth 32A on jaw member 5A when the two jaw members are brought together. Second movable jaw member 90A also includes a plurality of stepped surfaces 93A which are adapted to mate with stepped surfaces 38A on jaw member 5A when the two jaw members are brought together.

From the foregoing description, it will be obvious that first stationary jaw member 5A and second movable jaw member 90A can serve to grip tissue and/or objects between one another when they are brought together.

Figure 8:
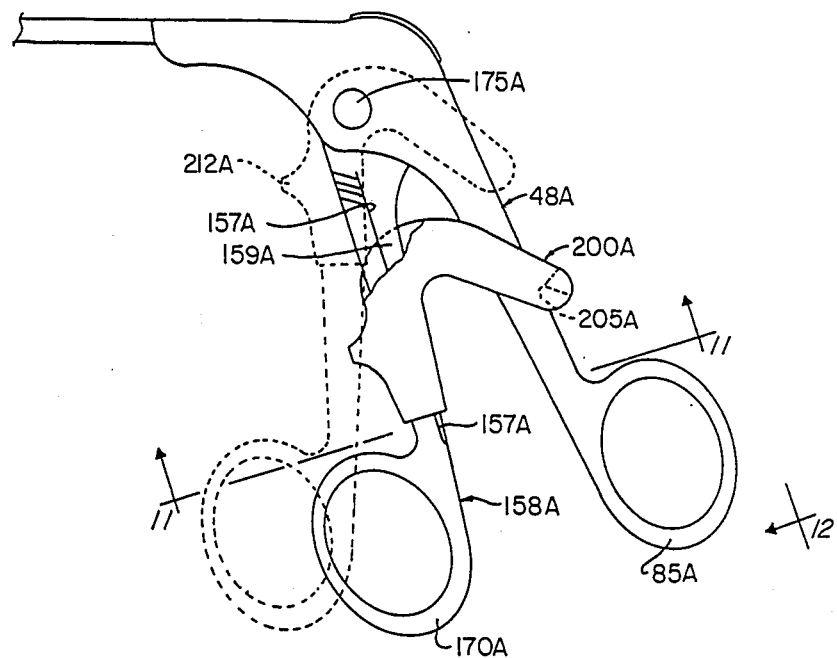
FIG. 8 is a partial elevational view of the left side of a surgical forceps which comprises another embodiment of the present invention, with the forceps being shown in their closed position by solid lines and in their open position by dotted lines.
Figure 11:
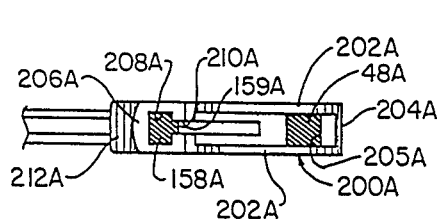
FIG. 11 is a sectional view taken along line 11—11 of FIG. 8.
Figure 12:
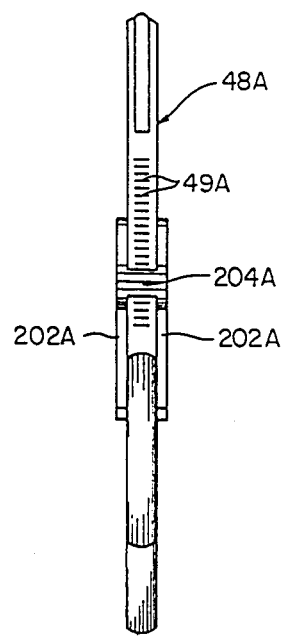
FIG. 12 is an end view in elevation taken along line 12—12 of FIG. 8.
Figure 10:
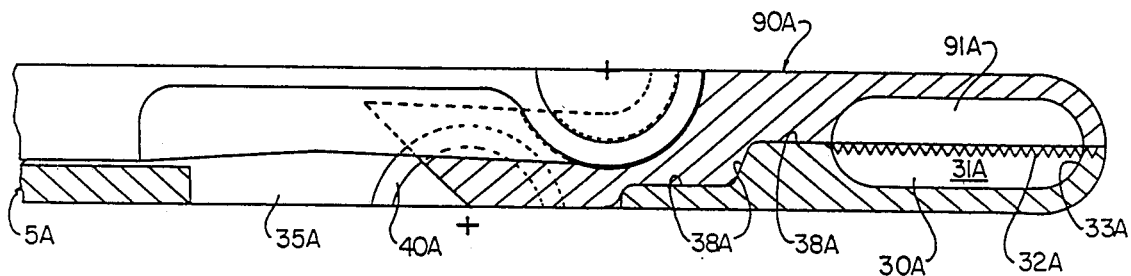
FIG. 10 is a view similar to FIG. 9 showing the same forceps in closed position.
Figure 9:
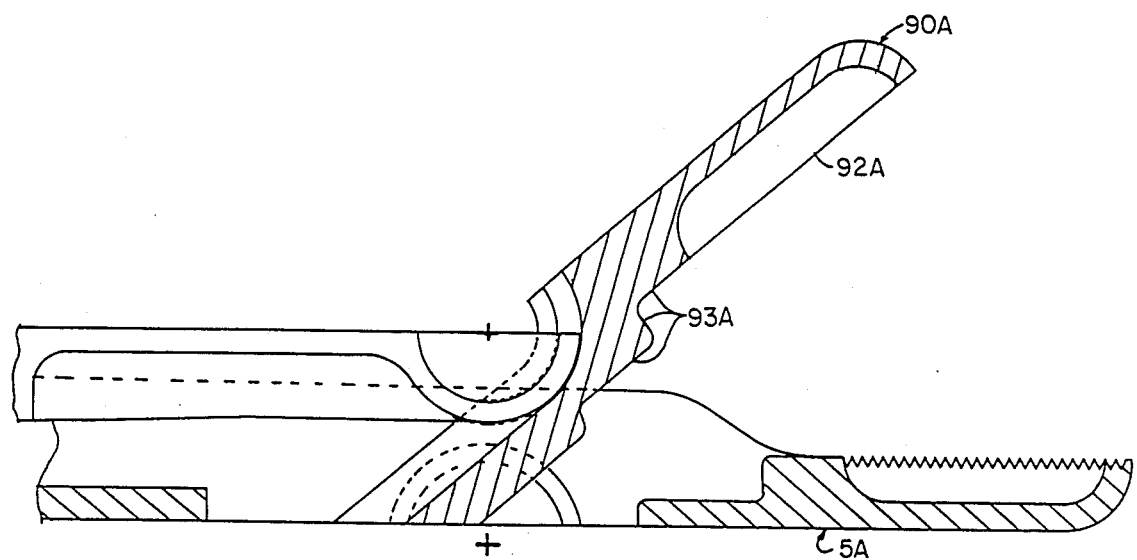
FIG. 9 is an enlarged fragmentary side elevation partially in section of the front portion of the forceps of FIG. 8 in open position.

The second way in which the forceps of FIGS. 8–12 depart from the design of the surgical punch of FIGS. 1–7 involves the tool's scissors-type handle. As shown in FIGS. 8, 11 and 12, the forceps of FIGS. 8–12 have a modified handle arrangement to accommodate locking means for keeping the jaws of the forceps in a selected position. More particularly, first arm 48A of the tool's scissors-type handle is substantially identical to first arm 48 of the surgical punch, except that a plurality of serrations 49A have been added on the rear surface of the arm. At the same time, second arm 158A of the scissors-type handle is substantially identical to second arm 158 of the surgical punch of FIGS. 1–7, except that the inner portion of arm 158A includes a pair of edge grooves 157A which form a rib 15gA of rectangular cross-section.

A locking member 200A is disposed on the scissors-type handle. Member 200A is of hollow construction, and includes a pair of side walls 202A formed integrally with a rear end section 204A and a front end section 206A. Front end section 206A is of C-shaped cross-section, and includes an interior hole 208A that accommodates arm 158A and a slot 210A that accommodates rib 159A. Additionally, locking member 200A has a front projection 212A that serves as a finger grip. Back section 204A is formed with a right angle corner edge 205A that is located so as to be able to be received in serrations 49A. The scissors arms 48A and 158A are arranged so that even when the jaws 5A and 90A are engaged with one another, the front and rear surfaces of the arms confronting the sections 204A and 206A diverge from one another with increasing distance from pivot pin 175A. Accordingly, when it is desired to lock the forceps, the locking member 200A is slipped down along arms 48A and 158A away from pivot point 175A as far as possible while squeezing the handles together. The latter will flex. When the lock member has moved to a point where it engages the serrations, the handles are relaxed, causing the corner edge 205A of the rear end section 204A to bite into serrations 49A. The lock member is in turn released by squeezing the handles together just enough to permit locking member 200A to be disengaged and moved upward toward pivot pin 175A.

The locking member's front projection 212A is sized and positioned so that when a user's thumb is engaged in finger grip 85A of first arm 48A, and the user's middle finger is engaged in finger grip 170A of second arm 158A, the user's index finger may engage projection 212A so as to force it to move up or down along the arms 48A and 158A of the scissors-type handle.

MODIFICATIONS OF THE PREFERRED EMBODIMENT

Of course, it is possible to modify the surgical punch and/or the surgical forceps previously described in a variety of ways without departing from the scope of the present invention.

Thus, for example, the surgical punch's first stationary jaw member 5 and its first arm 48 (or the surgical forceps' first stationary jaw member 5A and its first arm 48A) could be formed out of a single piece of metal, rather than out of several pieces as described and illustrated above.

Alternatively, the scissors-type handle of the surgical punch and/or the surgical forceps could be replaced by an entirely new type of handle, e.g. a pliers-type handle or a squeeze-type handle.

Furthermore, it is contemplated that the surgical punch (and/or the surgical forceps) could be modified so that the locations of grooves 40 and flanges 95 are reversed from those described and illustrated above, i.e., so that flanges 95 are disposed on first stationary arm 5 and grooves 40 are formed in second movable jaw member 90. Similarly, the surgical punch (and/or the surgical forceps) could be modified so that the locations of grooves 140 and flanges 155 are reversed from that described and illustrated above, i.e., so that flanges 155 are disposed on second movable jaw member 90 and grooves 140 are formed in coupling member 125.

It is also to be appreciated that the surgical punch (and/or the surgical forceps) could be modified so that second movable jaw member 90 moves downward relative to first stationary jaw member 5 when it opens and moves upward relative to first stationary jaw member 5 when it closes.

Figure 13:
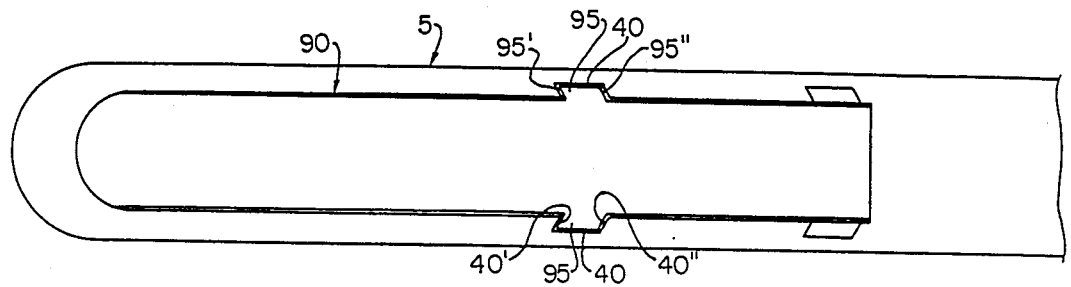
FIGS. 13-15 are enlarged bottom plan views of three modifications of the surgical punch of FIGS. 1-7; in each of FIGS. 13-15 the punch is in closed position.
Figure 14:
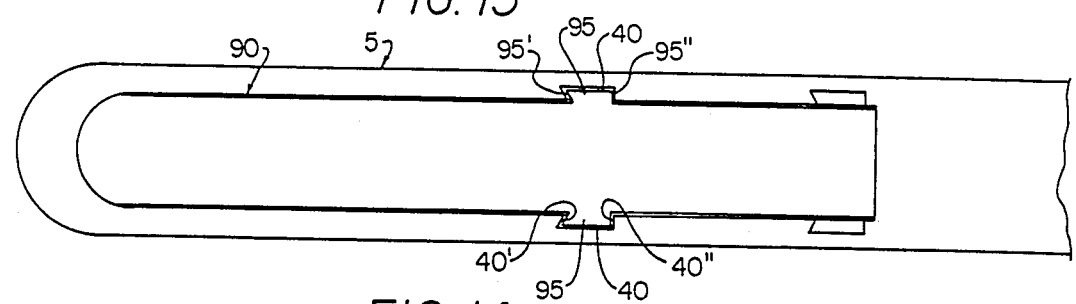
Figure 15:
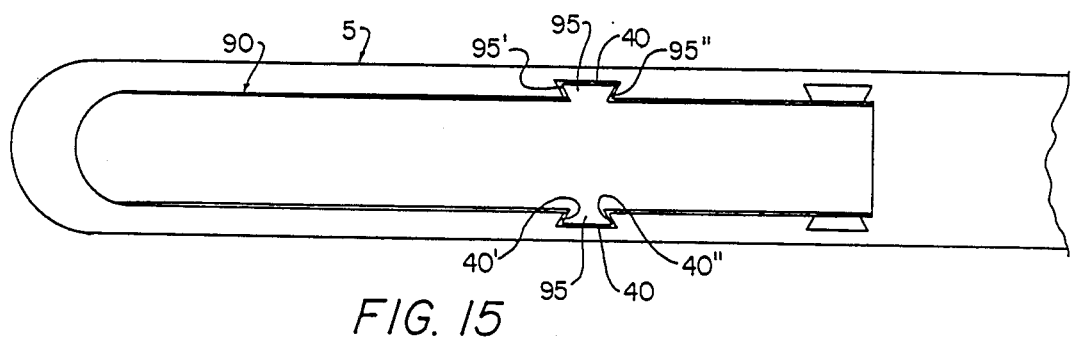

It is also contemplated that the surgical punch and/or the surgical forceps may be modified so that grooves 40 and flanges 95 have a configuration other than the simple right angle configuration previously described and illustrated. Referring to FIG. 7, in the embodiments heretofore disclosed, grooves 40 comprise a pair of opposing arcuate surfaces 40' and 40" which extend perpendicularly outward from inner surfaces 31, and flanges 95 comprise a pair of parallel arcuate surfaces 95' and 95" which extend perpendicularly outward from the outside walls of second movable jaw member 90. It is contemplated that the dispositions of surfaces 40' and 95" and/or 40" and 95" may be varied as, for example, shown in FIGS. 13–15. Thus, the constructions of grooves 40 and flanges 95 may be varied so that surfaces 40' and 40" (and also surfaces 95' and 95") remain parallel to one another but no longer extend outward at a right angle to inner surfaces 31. That modification is shown in FIG. 13. Alternatively, as shown in FIG. 14, the constructions of grooves 40 and flanges 95 may be changed so that one but not both of the surfaces 40' and 40" (and also surfaces g5' and g5") extends outward at a right angle to inner surfaces 31. Furthermore, as shown in FIG. 15, grooves 40 and flanges 95 may be modified so that surfaces 40' and 40" (and also surfaces 95' and 95") extend neither parallel to one another nor perpendicularly outward from inner surfaces 31.

Another possible modification is to form the jaws of the surgical forceps with a shape somewhat different from the one described and illustrated above. Thus, for example, the bottom surface 92A (FIG. 10) of movable jaw member 90A could be formed with a plurality of tiny teeth sized and shaped to mate with teeth 32A on jaw member 5A when the two jaw members are brought together. Another possible change is to omit teeth 32 from the lower jaw member and replace them with a flat surface, so that the movable jaw member's flat surface 92A engages a like flat surface on the lower jaw member when the two jaw members are brought into engagement with one another. Furthermore, the two jaw members could be provided with long, spike-like teeth that mesh when the two jaw members close, or with surfaces adapted to form a conventional tongue-and-groove arrangement when the two jaw members close.

Figure 16:
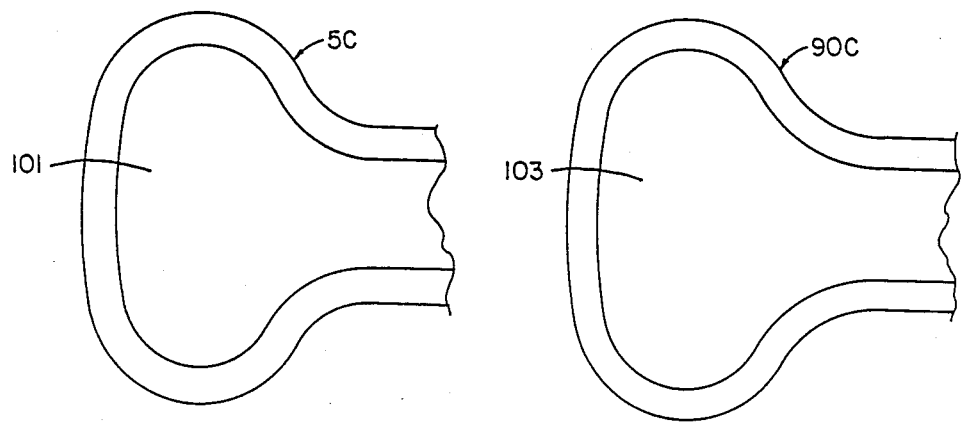
FIG. 16 is an enlarged top plan view of the front portion of a modification of the surgical forceps.
Figure 17:
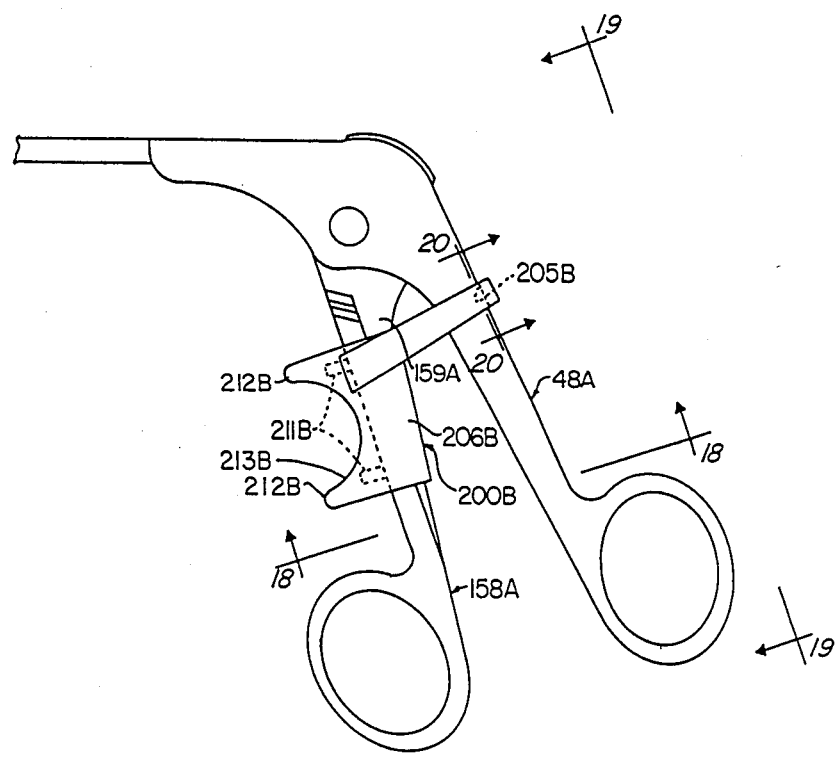
FIG. 17 is a view similar to FIG. 8 of a forceps design constituting still another embodiment of the present invention, with the forceps being shown in their closed position.
Figure 18:
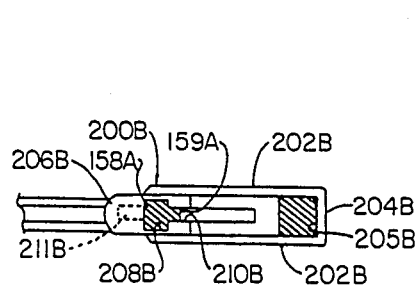
FIG. 18 is a sectional view taken along line 18—18 of FIG. 17.

Still another possible modification comprises forming the two jaw members so that one or both is substantially spoon-like in character, in the manner illustrated in FIG. 16 where members 101 and 103 represent the curved bowl-like portions of the two spoon-shaped jaw members 5C and 90C. This latter design enhances the use of the forceps in retrieving tiny objects (e.g. calcium deposits, bone chips, etc.).

Figure 20:
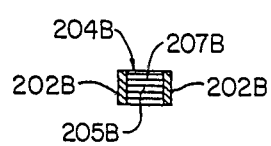
FIG. 20 is a sectional view taken along line 20—20 of FIG. 17.
Figure 19:
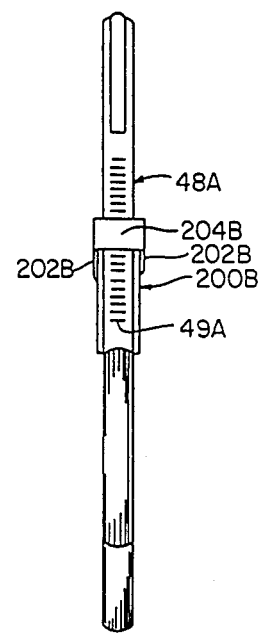
FIG. 19 is an end view in elevation taken along line 19—19 of FIG. 17.

A further novel feature of the invention is a modification of the forceps' locking member shown in FIGS. 17-20. In this case the alternative form of locking member 200B includes a pair of side walls 202B which are formed integrally with a rear connecting wall section 204B. Side walls 202B are attached to a front section 206B, e.g. by brazing. Front end section 206B is of C-shaped cross-section, and includes (1) an interior hole 208B that accommodates arm 158A and (2) a slot 210B that accommodates rib 159A. Teflon bushings 211B are disposed in front end section 206B so that they bear against the front surface of arm 158A and thereby enhance the movement of locking member 200B along arm 158A. Locking member 200B also has a pair of front projections 212B terminating in a curved surface 213B and coacting therewith to form a finger grip. Back section 204B is formed with a planar front surface 205B which has a plurality of serrations 207B formed therein (FIG. 20). Serrations 207B engage the serrations 49A of arm 48A as the locking member is moved downward along the scissors-type handle. Operation of locking member 200B is substantially the same as the operation of the aforementioned locking member 200A.

Still other modifications are well within the skill of the art and considered to be part of the present invention.

ADVANTAGES OF THE INVENTION

Numerous advantages are gained by the present invention. First, it allows a surgical punch and forceps to be produced which are extremely durable and able to withstand significant stress during use without failing. Second, the new surgical punch or forceps utilizes a relatively efficient mechanical design wherein the pivot points are subjected to a minimum of stress during use. Third, the surgical punch or forceps totally avoids the use of fragile pivot pins in its construction. Fourth, the present invention allows construction of surgical punches and forceps that are relatively small and work well in confined spaces. Fifth, the surgical punch utilizes a design whereby its cutting action is a combination of shearing and cutting, rather than just shearing alone. Sixth, the surgical forceps have novel locking means which can accurately lock the forceps in position for an extended period of time. And seventh, the present invention provides forceps which may be used in areas other than the medical field, e.g. in the electronics industry, the jewelry industry, etc. Still other advantages will be obvious to persons skilled in the art.

What I claim is:

1. A surgical punch comprising a first stationary jaw member, a second movable jaw member, and a coupling member that is movable relative to said first stationary jaw member, one of said jaw members comprising at least one first arcuate flange and the other of said jaw members comprising at least one first arcuate groove, said at least one first arcuate flange being slidably disposed in said at least one first arcuate groove so as to pivotally couple said second movable jaw member to said first stationary jaw member, whereby said second movable jaw member is capable of pivotal movement towards and away from said first stationary jaw member, with said at least one first arcuate flange and said at least one first arcuate groove having a first center of curvature that is fixed in position relative to said first stationary jaw member when said at least one first arcuate flange is disposed in said at least one first arcuate groove, and one of said second movable jaw member and said coupling member comprising at least one second arcuate flange and the other of said second movable jaw member and said coupling member comprising at least one second arcuate groove, said at least one second arcuate flange being slidably disposed in said at least one second arcuate groove so as to pivotally couple said coupling member to said second movable jaw member, with said at least one second arcuate flange and said at least one second arcuate groove having a second center of curvature that is fixed in position relative to said coupling member and is not fixed in position relative to said first stationary jaw member when said at least one second arcuate flange is disposed in said at least one second arcuate groove, and one of said centers of curvature is displaced laterally from said stationary jaw member and said coupling member, whereby (a) when said coupling member is moved in a first direction relative to said first stationary jaw member, said second movable jaw member will open away from said first stationary jaw member, and (b) when said coupling member is moved in a second opposite direction relative to said first stationary jaw member, said second movable jaw member will close towards said first stationary jaw member, said first and second jaw members being arranged so that body tissue located between said first and second jaw members may be severed in a punching motion as said jaw members are opened and closed relative to one another by movement of said coupling member relative to said first stationary jaw member.

2. A surgical punch according to claim 1 wherein said first stationary jaw member has an opening, and further wherein said second movable jaw member is moved into said opening when said coupling member is moved in said second opposite direction, whereby said first stationary jaw member serves as a die and said second movable jaw member serves as a punch to cut tissue disposed between said two jaw members.

3. A surgical punch according to claim 1 wherein said first and second centers of curvature lie on first and second axes of rotation, respectively, that extend parallel to one another and perpendicular to said first and second directions.

4. A surgical punch according to claim 3 wherein said at least one first arcuate groove is formed in said first stationary jaw member, and said at least one first arcuate flange is formed on said second movable jaw member.

5. A surgical punch according to claim 4 wherein said first stationary jaw member has two aligned and mutually spaced first arcuate grooves formed therein, and said second movable jaw member has two aligned and mutually spaced first arcuate flanges formed thereon, with said two first arcuate flanges being slidably disposed in said two first arcuate grooves.

6. A surgical punch according to claim 3 wherein said first stationary jaw member is attached to one arm of a scissors-type handle, and said coupling member is attached to a second arm of said scissors-type handle.

7. A surgical punch according to claim 3 wherein said at least one second arcuate groove is formed in said second movable jaw member, and said at least one second arcuate flange is formed on said coupling member.

8. A surgical punch according to claim 7 wherein said second movable jaw member has two aligned and mutually spaced second arcuate grooves formed therein, and said coupling member has two aligned and mutually spaced second arcuate flanges formed thereon, with said two second arcuate flanges being slidably disposed in said two second arcuate grooves.

9. A surgical punch according to claim 8 wherein said second movable jaw member has a longitudinal recess dividing said jaw member into first and second portions, and further wherein one of said second arcuate grooves is formed in said first portion and the other of said second arcuate grooves is formed in said second portion of said second movable jaw member.

10. A surgical punch according to claim 3 wherein said first and second jaws are elongated in a direction parallel to said first and second directions.

11. A surgical punch according to claim 3 wherein said at least one first arcuate groove, said at least one first arcuate flange, said at least one second arcuate groove and said at least one second arcuate flange are all circularly curved.

12. A surgical punch according to claim 3 wherein said first center of curvature is displaced from said first stationary jaw member.

13. A surgical punch according to claim 3 wherein said second center of curvature is displaced from said coupling member.

14. A surgical punch according to claim 3 wherein when said coupling member is moved in said second direction so as to close said jaw members relative to one another, said at least one first arcuate flange and said at least one first arcuate groove are spaced from said at least one second arcuate flange and said at least one second arcuate groove in a direction extending transversely to said first and second directions.

15. Surgical forceps according to claim 14 wherein said first and second centers of curvature lie on first and second axis of rotation respectively, that extend parallel to one another and perpendicular to said first and second directions.

16. Surgical forceps according to claim 15 wherein said at least one first arcuate groove is formed in said first stationary jaw member, and said at least one first arcuate flange is formed on said second movable jaw member.

17. Surgical forceps according to claim 16 wherein said first stationary jaw member has two aligned and mutually spaced first arcuate grooves formed therein, and said second movable jaw member has two aligned and mutually spaced first arcuate flanges formed thereon, with said two first arcuate flanges being slidably disposed in said two first arcuate grooves.

18. Surgical forceps according to claim 15 wherein said at least one second arcuate groove is formed in said second movable jaw member, and said at least one second arcuate flange is formed on said coupling member.

19. Surgical forceps according to claim 18 wherein said second movable jaw member has two aligned and mutually spaced second arcuate grooves formed therein, and said coupling member has two aligned and mutually spaced second arcuate flanges formed thereon, with said two second arcuate flanges being slidably disposed in said two second arcuate grooves.

20. Surgical forceps according to claim 19 wherein said second movable jaw member has a longitudinal recess dividing said jaw member into first and second portions, and further wherein none of said second arcuate grooves is formed in said first portion and the other of said second arcuate grooves is formed in said second portion of said second movable jaw member.

21. Surgical forceps according to claim 15 wherein said first and second jaws are elongated in a direction parallel to said first and second directions.

22. Surgical forceps according to claim 15 wherein said at least one first arcuate groove, said at least one first arcuate flange, said at least one second arcuate groove and said at least one second arcuate flange are all circularly curved.

23. Surgical forceps according to claim 15 wherein said first center of curvature is displaced from said first stationary jaw member.

24. Surgical forceps according to claim 15 wherein said second center of curvature is displaced from said coupling member.

25. Surgical forceps according to claim 15 wherein when said coupling member is moved in said second direction so as to close said jaw members relative to one another, said at least one first arcuate flange and said at least one first arcuate groove are spaced from said at least one second arcuate flange and said at least one second arcutate groove in a direction extending transversely to said first and second directions.

26. Surgical forceps according to claim 15 wherein said at least one first arcuate flange and said at least one first arcuate groove are dovetailed.

27. Surgical forceps according to claim 26 wherein said at least one first arcuate groove is defined by at least one surface that extends neither parallel to nor perpendicular to said first axes of rotation.

28. Surgical forceps according to claim 26 wherein said at least one first arcuate groove is defined by a pair of surfaces, and further wherein said surfaces extend parallel to one another.

29. Surgical forceps according to claim 26 wherein said at least one first arcuate groove is defined by a pair of surfaces, and further wherein said surfaces converge towards one another.

30. Surgical forceps according to claim 15 wherein said first stationary jaw member comprises a longitudinal groove, and further wherein said coupling member rides within said longitudinal groove as said second movable jaw member moves relative to said first stationary jaw member.

31. Surgical forceps according to claim 15 wherein said first center of curvature is displaced from said first stationary jaw member and said second center of curvature is displaced from said coupling member.

32. A surgical punch according to claim 3 wherein said at least one first arcuate flange and said at least one first arcuate groove are dovetailed.

33. A surgical punch according to claim 32 wherein said at least one first arcuate groove is defined by at least one surface that extends neither parallel to nor perpendicular to said first axis of rotation.

34. A surgical punch according to claim 32 wherein said at least one first arcuate groove is defined by a pair of surfaces, and further wherein said surfaces extend parallel to one another.

35. A surgical punch according to claim 32 wherein said at least one first arcuate groove is defined by a pair of surfaces, and further wherein said surfaces converge towards one another.

36. A surgical punch according to claim 3 wherein said first stationary jaw member comprises a longitudinal groove, and further wherein said coupling member rides within said longitudinal groove as said second movable jaw member moves relative to said first stationary jaw member.

37. A surgical punch according to claim 3 wherein said first center of curvature is displaced from said first stationary jaw member and said second center of curvature is displaced from said coupling member.

38. Surgical forceps comprising a first stationary jaw member, a second movable jaw member, and a coupling member that is movable relative to said first stationary jaw member, one of said jaw members comprising at least one first arcuate flange and the other of said jaw members comprising at least one first arcuate groove, said at least one first arcuate flange being slidably disposed in said at least one first arcuate groove so as to pivotally couple said second movable jaw member to said first stationary jaw member, whereby said second movable jaw member is capable of pivotal movement towards and away from said first stationary jaw member, with said at least one first arcuate flange and said at least one first arcuate groove having a first center of curvature that is fixed in position relative to said first stationary jaw member when said at least one first arcuate flange is disposed in said at least one first arcuate groove, and one of said second movable jaw member and said coupling member comprising at least one second arcuate flange and the other of said second movable jaw member and said coupling member comprising at least one second arcuate groove, said at least one second arcuate flange being slidably disposed in said at least one second arcuate groove so as to pivotally couple said coupling member to said second movable jaw member, with said at least one second arcuate flange and said at least one second arcuate groove having a second center of curvature that is fixed in position relative to said coupling member and is not fixed in position relative to said first stationary jaw member when said at least one second arcuate flange is disposed in said at least one second arcuate groove, and one of said centers of curvature is displaced laterally from said first stationary jaw member and said coupling member, whereby (a) when said coupling member is moved in a first direction relative to said first stationary jaw member, said second movable jaw member will open away from said first stationary jaw member, and (b) when said coupling member is moved in a second opposite direction relative to said first stationary jaw member, said second movable jaw member will close towards said first stationary jaw member, said jaw members having mutually confronting surfaces for engaging and clamping body tissue or other material therebetween as said jaw members are closed relative to one another.

39. Surgical forceps according to claim 38 wherein at least one of said mutually confronting surfaces of said jaw members is serrated to facilitate gripping tissue or other material which is clamped therebetween.

40. Surgical forceps according to claim 38 wherein said first stationary jaw member is attached to one arm of a scissor-type handle, and said coupling member is attached to a second arm of said scissors-type handle.

41. Surgical forceps according to claim 40 further including locking means carried by said scissors-type handle for releasably locking said first and second arms against movement so as to hold said jaw members in a selected position relative to one another.

42. Surgical forceps according to claim 41 wherein said locking means comprises a member which embraces said first and second arms and is movable lengthwise of said arms.

43. Surgical forceps according to claim 42 wherein said locking means cooperates with serrations on one of said arms to hold it in a selected locking position on said arm.

* * * * *

UNITED STATES PATENT AND TRADEMARK OFFICE
CERTIFICATE OF CORRECTION

PATENT NO. : 4,712,545
DATED : December 15, 1987
INVENTOR(S) : George P. Honkanen It is certified that error appears in the above-identified patent and that said Letters Patent is hereby corrected as shown below:

Claim 1, col. 10, line 16, the term "moba-" should be changed to -- mova- --;

Claim 15, col. 11, line 48, the number "14" should be changed to -- 38 --;

Claim 15, col. 11, line 50, the word "axis" should be changed to -- axes --;

Claim 15, col. 11, line 50, after the word "rotation" insert -- , --;

Claim 20, col. 12, line 11, the word "none" should be changed to -- one --;

Claim 25, col. 12, line 35, the word "arcutate" should be changed to -- arcuate --;

Claim 27, col. 12, line 43, the word "axes" should be changed to -- axis --;

Claim 28, col. 12, line 44, the word "acording" should be changed to -- according --; and

UNITED STATES PATENT AND TRADEMARK OFFICE
CERTIFICATE OF CORRECTION

PATENT NO. : 4,712,545
DATED : December 15, 1987
INVENTOR(S) : George P. Honkanen It is certified that error appears in the above-identified patent and that said Letters Patent is hereby corrected as shown below:

Claim 40, col. 14, line 30, the term "scissor-type" should be changed to -- scissors-type --.

Signed and Sealed this

Second Day of August, 1988

Attest:

DONALD J. QUIGG

*Attesting Officer*  *Commissioner of Patents and Trademarks*